United States Patent
Seo et al.

(10) Patent No.: US 8,628,944 B2
(45) Date of Patent: Jan. 14, 2014

(54) METHOD FOR PRODUCING ETHANOL FROM XYLOSE

(75) Inventors: Jin-Ho Seo, Seoul (KR); Yong-Cheol Park, Seoul (KR)

(73) Assignee: SNU R&DB Foundation, Seoul (KR)

( * ) Notice: Subject to any disclaimer, the term of this patent is extended or adjusted under 35 U.S.C. 154(b) by 327 days.

(21) Appl. No.: 12/815,837

(22) Filed: Jun. 15, 2010

(65) Prior Publication Data

US 2011/0143409 A1 Jun. 16, 2011

Related U.S. Application Data

(63) Continuation of application No. PCT/KR2009/007458, filed on Dec. 12, 2009.

(51) Int. Cl.
*C12P 7/06* (2006.01)

(52) U.S. Cl.
USPC ........ 435/161; 433/252; 433/320.1; 433/161; 433/7.1

(58) Field of Classification Search
None
See application file for complete search history.

(56) References Cited

PUBLICATIONS

Ni et al. (AEM Accepts, Feb. 2007, pp. 1-245).*
Watanabe et al. (Microbiology, 2007, vol. 153, pp. 3044-3054).*
International Search Report for PCT/KR2009/007458 mailed Aug. 5, 2010.
Bengtsson et al., "Xylose reductase from *Pichia stipitis* with altered coenzyme preference improves ethanolic xylose fermentation by recombinant *Saccharomyces cerevisiae*", Biotechnology for Biofuels 2009, 2:9.
Prasad et al., "Ethanol as an alternative fuel from agricultural, inductrial and urban residues", Resources, Conservation and Recycling 50 (2007) 1-39.

* cited by examiner

*Primary Examiner* — Hope Robinson
(74) *Attorney, Agent, or Firm* — Edwards Wildman Palmer LLP

(57) ABSTRACT

Disclosed is a method for producing ethanol from xylose using a recombinant *Saccharomyces cerevisiae* strain transformed to express a xylose reductase that uses NADH as a cofactor and a xylitol dehydrogenase that uses NAD+ as a cofactor, which are coupled with each other. The method provides an increase in ethanol yield and production efficiency, as compared to a control group, and enables production of ethanol at higher yield and high production efficiency by further eliminating acetaldehyde dehydrogenase which mediates production of acetic acid (by-product).

4 Claims, 5 Drawing Sheets

\* Level: u/mg-Protein 1 (*S. cerevisiae*) D452-2

2 (*S. cerevisiae*) D452-2/pXR$^{WT}$/pXDH (Multiple copies)

3 (*S. cerevisiae*) D452-2/pXR$^{MUT}$/pXDH (Multiple copies)

4 (*S. cerevisiae*) D452-2 YIpXR$^{MUT}$-XDH (Single copy)

METHOD FOR PRODUCING ETHANOL FROM XYLOSE

CROSS-REFERENCE TO RELATED APPLICATION

This application is a continuation of PCT/KR2009/007458 filed Dec. 12, 2009, the entire contents of which are incorporated herein by reference.

TECHNICAL FIELD

The present invention relates to a method for producing ethanol from xylose using recombinant *Saccharomyces cerevisiae*. More particularly, the present invention relates to a method for producing ethanol from xylose using recombinant *Saccharomyces cerevisiae* wherein the recombinant *Saccharomyces cerevisiae* is transformed such that NADH and NAD+ as cofactors are coupled with each other and used, and that acetaldehyde dehydrogenase producing acetic acid is not expressed.

BACKGROUND ART

Ethanol, the main ingredient in alcoholic beverages, has been consumed since the development of alcoholic beverages. However, in modern times, ethanol is attracting considerable attention as a clean energy alternative to petroleum. In Brazil, ethanol has been commercialized as a fuel for transportation for a long time. Ethanol fuels, consisting of 10% ethanol and 90% gasoline, are commercially available in the U.S.A.

Meanwhile, at the conventional low-cost oil age involving cheap petroleum, the cost of manufacturing ethanol is higher than the price of oil, and thus ethanol is not cost-competitive. However, taking into consideration gradual exhaustion of oil deposits and increased oil prices, ethanol is becoming increasingly cost-competitive and will eventually overtake the price competitiveness of petroleum.

Ethanol used as a transportation fuel is prepared from sugarcane, corn, etc. Sugarcane is a raw material of sugar and corn is a raw material of foods. For this reason, the use of these sources for the preparation of ethanol causes, as a side-effect, an increase in sugar or corn costs and, as an ethical problem, use of the grain for fuel materials, rather than food materials.

Accordingly, a great deal of research is widely conducted on the development of alternatives to sugarcane and corn. Xylose, found at high concentrations in waste wood materials or forestry by-products, is one potential candidate.

Xylose, a form of biomass, is found at high concentrations in wood waste in the form of polymeric xylene. Xylose is separated from xylo-oligosaccharide (XOS) formed through hydrolysis of xylan, which is used for the preparation of xylitol capable of preventing dental caries.

Xylose is a renewable resource, which is recovered from wood byproducts generated in the process of producing pulp, etc. Use of xylose does not entail an increase in alternative material prices and is free from ethical problems and a great deal of research associated therewith is thus conducted at present.

Meanwhile, *Saccharomyces cerevisiae* is well-known as a strain for producing ethanol in the preparation of fermented liquor such as coarse liquor. *Saccharomyces cerevisiae* is actively utilized as a host for the preparation of useful medicines and its use as a host for preparing ethanol is actively researched.

*Saccharomyces cerevisiae* has neither xylose reductase (XR) nor xylitol dehydrogenase (XDH) and thus, disadvantageously, cannot metabolize xylose.

Accordingly, in order to allow *Saccharomyces cerevisiae* to metabolize xylose, a great deal of research is being conducted into incorporation of these enzymes into *Saccharomyces cerevisiae*. From research results, it can be confirmed that xylose is substantially metabolized.

In addition, when *Saccharomyces cerevisiae* metabolizes xylose, ethanol is produced as a byproduct. Accordingly, some researchers have attempted to produce ethanol coming into the spotlight as an alternative energy using *Saccharomyces cerevisiae*.

In this regard, the preparation of ethanol from xylose causes problems of low preparation yield and low economic efficiency. These problems are also caused by limited supply of NAD(P)H and NAD (P)+, as cofactors, and acetic acid obtained as a by-product.

SUMMARY OF THE DISCLOSURE

Therefore, the present invention has been made in view of the above problems, and it is an object of the present invention to develop and provide a method for preparing ethanol from xylose using recombinant *Saccharomyces cerevisiae* to solve supply bottleneck of NADH or NAD+ as a cofactor and minimize preparation of acetic acid, and thereby increase an amount of ethanol produced.

In accordance with the present invention, the above and other objects can be accomplished by the provision of a method for preparing ethanol from xylose using recombinant *Saccharomyces cerevisiae* wherein the recombinant *Saccharomyces cerevisiae* is transformed to express xylose reductase (XR) converting xylose into xylitol using NADH as a cofactor; wherein the recombinant *Saccharomyces cerevisiae* is transformed to express xylitol dehydrogenase (XDH) converting xylitol into xylulose using NAD+ as a cofactor; wherein the recombinant *Saccharomyces cerevisiae* is transformed to over-express xylulokinase (XK) converting xylulose into xylulose 5-phosphate; and wherein the recombinant *Saccharomyces cerevisiae* is transformed to over-express transaldolase 1 (TAL1) converting sedoheptulose 7-phosphate and glyceraldehyde 3-phosphate into erythrose 4-phosphate and fructose 6-phosphate (See FIG. 1).

*Saccharomyces cerevisiae* is commercially available as an ethanol-producing strain, but does not utilize xylose as a sole carbon source. This is because *Saccharomyces cerevisiae* has neither xylose reductase (XR) nor xylitol dehydrogenase (XDH), thus having no metabolic ability to convert xylose into xylulose. Accordingly, XR and XDH enzymes should be incorporated into hosts in order to produce ethanol. Generally, XR utilizes NADPH as a cofactor and XDH utilizes NAD+ as a cofactor.

In the present invention, NADH-preferring XR, rather than NADPH-dependent XR, is incorporated and coupled with NAD+-dependent XDH. When NADH and NAD+ as cofactors are coupled with each other, they are reproduced and reusable, thus solving the problem, namely, deterioration in economic efficiency, which is caused by limited cofactor supply.

In the *Saccharomyces cerevisiae* transformed by incorporating XR and XDH, xylose is converted into xylulose by the NADH-preferring XR and NAD+-dependent XDH, and xylulose is converted into xylulose 5-phosphate by the additionally-incorporated XK and metabolized through pentose phosphate pathway.

When XK is not over-expressed, although it is an enzyme present in yeast, and XR and XDH are incorporated into strains, ethanol can be produced from xylose, but yield and production efficiency are considerably low. Accordingly, it is preferred that XK be over-expressed.

Meanwhile, transaldolase 1 (TAL1) is an enzyme present on the pentose phosphate pathway, which converts sedoheptulose 7-phosphate and glyceraldehyde 3-phosphate into 4-erythrose 4-phosphate and fructose 6-phosphate. In the present invention, TAL1 is over-expressed in order to improve production efficiency of ethanol.

Meanwhile, in the present invention, a recombinant *Saccharomyces cerevisiae* wherein xylose reductase or xylitol dehydrogenase is integrated into the genome of *Saccharomyces cerevisiae* is preferred. When genes are incorporated into the genome, they are advantageously not lost during culturing.

Meanwhile, the recombinant *Saccharomyces cerevisiae* wherein xylulokinase (XK) is integrated into delta sequences on the genome of *Saccharomyces cerevisiae* is preferred, since it is can be integrated in the form of multiple copies.

Meanwhile, the recombinant *Saccharomyces cerevisiae* is preferably transformed such that it does not express acetaldehyde dehydrogenase to convert acetaldehyde into acetic acid. This is the reason that production of acetic acid, as a by-product, is prevented and ethanol can thus be produced with a high yield and high production efficiency. At this time, the transformation of the recombinant *Saccharomyces cerevisiae* such that acetaldehyde dehydrogenase is not expressed can be preferably carried out by entirely or partially fragmenting acetaldehyde dehydrogenase-encoding genes.

Meanwhile, the production of the recombinant *Saccharomyces cerevisiae* which is additionally transformed, such that acetaldehyde dehydrogenase is not expressed, is preferably carried out by $O_2$-limited fed-batch fermentation. The reason for the $O_2$-limited fed-batch fermentation is that the production of acetic acid as a by-product is minimized.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE DISCLOSURE

As apparent from the above description, the present invention provides a method for producing ethanol using *Saccharomyces cerevisiae*, wherein NADH as a cofactor of xylose reductase required for ethanol production, and $NAD^+$ as a cofactor of xylitol dehydrogenase are coupled and utilized and acetaldehyde dehydrogenase mediating production of acetic acid as a byproduct is removed, and ethanol can thus be produced at a high yield and high production efficiency.

Hereinafter, the following Examples and Experimental Examples will be provided for a further understanding of the invention. The following examples are for illustrative purposes only and are not intended to limit the scope of the present invention.

Example 1

Production of Transformed *Saccharomyces cerevisiae* Strains

In this example, recombinant *Saccharomyces cerevisiae* used for the following Examples 2 to 4 were prepared.

Meanwhile, gene recombinant is not described in detail in this example. Gene recombination and methods for producing transformation systems are well-known in the art, genetic engineering, and a detailed description thereof is thus omitted.

The *Saccharomyces cerevisiae* D452-2 used herein as a host was obtained from professor Makino of Kyoto University in Japan (Seiya Watanabe, Ahmed Abu Saleh, Seung Pil Pack, Narayana Annaluru, Tsutomu Kodaki and Keisuke Makino. 2007. Ethanol production from xylose using recombinant *Saccharomyces cerevisiae* expressing protein-engineered NADH-preferring xylose reductase from *Pichia stipitis*. Microbiol. 153:3044-3054).

Figure 1:
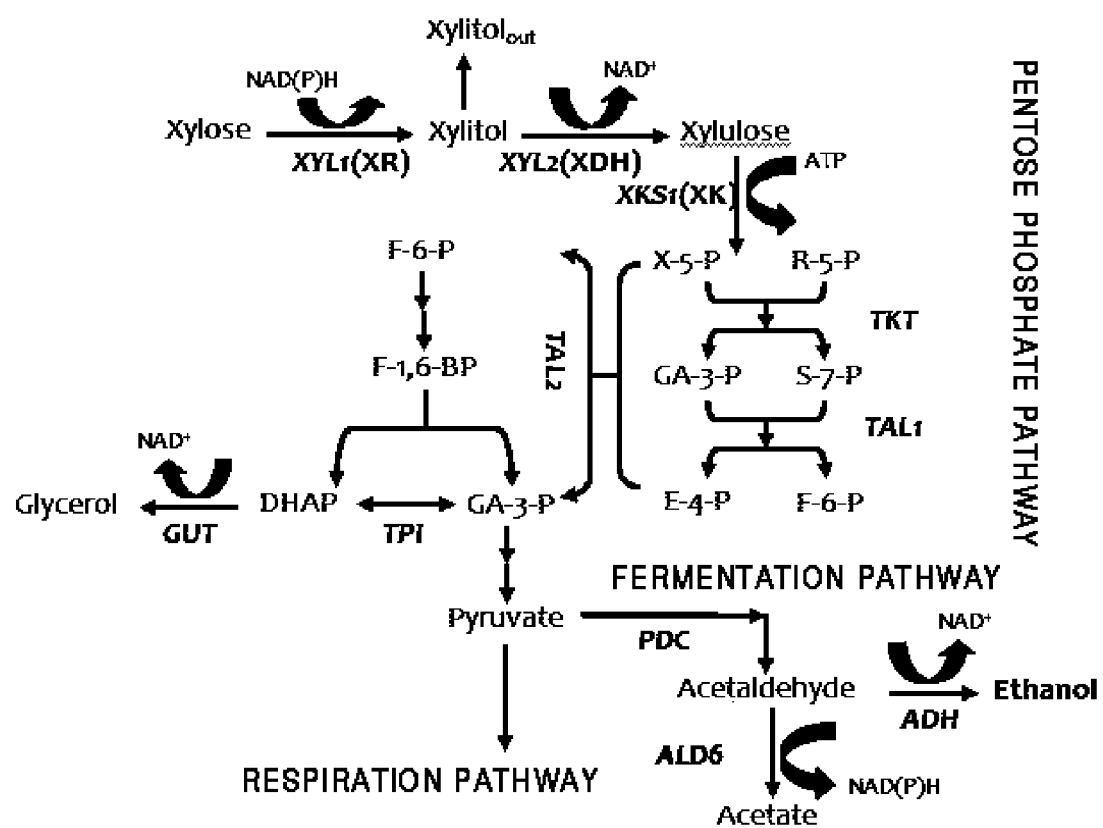
FIG. 1 is a flow chart illustrating a process for producing ethanol from xylose according to the present invention.
Figure 2:
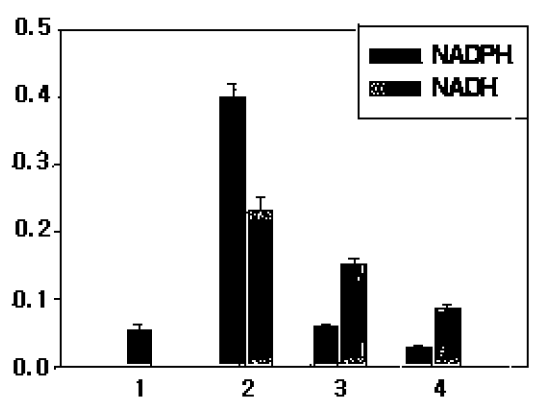
FIG. 2 is a graph showing the fact that the mutated XR, unlike the wild-type XR, exhibits high affinity for NADH over NADPH.

Vectors, YEpM4XR(WT), YEpM4XR(R276H) and pPGKXDH(WT) were also collected from professor Makino of Kyoto University in Japan and the XR(R276H) enzyme mutated by subjecting wild-type XR to point mutation exhibits higher selective affinity for NADH over NADPH, as compared to wild-type XR (See FIG. 2, Seiya Watanabe, Ahmed Abu Saleh, Seung Pil Pack, Narayana Annaluru, Tsutomu Kodaki and Keisuke Makino. 2007. Ethanol production from xylose by recombinant *Saccharomyces cerevisiae* expressing protein-engineered NADH-preferring xylose reductase from *Pichia stipitis* Microbiol. 153:3044-3054).

The parent vectors for the production of YIpXRWT-XDHWT and YEpM4XR(R276H), YIp5 and delta ISXK, were collected from Tae-Hee Lee, previous researcher, the Graduate School of Seoul National University (Tae-Hee Lee, Metabolic engineering studies on production of ethanol from xylose by recombinant *Saccharomyces cerevisiae*, M. S. Thesis, Seoul National University, 2000).

The parent vector used for the production of pAUR_d_ALD6, pAUR101, was a vector which is commercially obtainable from Takara, Japan, and ALD6 genes were obtained by cloning from *S. cerevisiae* CEN.PK2-1D.

The TAL1 genes were obtained by cloning *Pichia stipitis* CBS6054.

Table 1 below shows strains produced in this example and gene types thereof.

TABLE 1

| Strains prepared in this example | | |
|---|---|---|
| Strains | Gene type | Plasmids used |
| D452-2 | Matα, leu2 his3 ura3 can1 | |
| D452-2/ pXR$^{WT}$/pXDH | D452-2, ura3::URA3, leu2::LEU2 YEpM4XR(WT), pPGKXDH(WT) | YEpM4XR(WT), pPGKXDH(WT) |
| D452-2/ pXR$^{MUT}$/pXDH | D452-2, ura3::URA3, leu2::LEU2, YEpM4XR(R276H), pPGKXDH(WT) | YEpM4XR(R276H), pPGKXDH(WT) |

TABLE 1-continued

Strains prepared in this example

| Strains | Gene type | Plasmids used |
|---|---|---|
| D452-2/ YIpXR$^{WT}$-XDH | D452-2, ura3::URA3 $P_{PGK}$-XYL1$^{WT}$-T$_{PGK}$, $P_{PGK}$-XYL2$^{WT}$-T$_{PGK}$ | YIpXR$^{WT}$-XDH$^{WT}$ |
| SX2 | D452-2, ura3::URA3 $P_{PGK}$-XYL1$^{MUT}$-T$_{PGK}$, $P_{PGK}$-XYL2$^{WT}$-T$_{PGK}$ | YIpXR$^{R276H}$-XDH$^{WT}$ |
| SX3 | SX2, Ty1-delta::P$_{GPD}$-XKS1-T$_{GPD}$-neo$^r$ | delta ISXK |
| SX5 | SX3, , leu2::LEU2 YEpM4XR(R276H), p423PsTAL1 | YEpM4XR(R276H), P423PsTAL1 |
| SX5:ald6☐ | SX5, ALD6::pAUR_d_ALD6 | pAUR_d_ALD6 |

1) WT: wild type

Example 2

Fermentation of Xylose Using NADH-Preferring XR Rather than NADPH-Dependent XR In order to confirm the effects of the fermentation using a NADH-dependent XR mutant (hereinafter, also referred to as "XR$^{mut}$"), rather than NADPH-dependent XR, on the metabolism of xylose, the following experiments were performed.

The strain used herein was D452-2/pXR$^{MUT}$/pXDH into which XR$^{mut}$ and XDH are episomally integrated in the form of plasmids. The substrate used herein was xylose and aerobic fermentation was performed. D452-2/pXR$^{WT}$/pXDH into which wild-type NADPH-dependent XR (hereinafter, referred to as "XR$^{WT}$") and XDH are episomally integrated in the form of plasmids was used as a control group strain.

Figure 3:
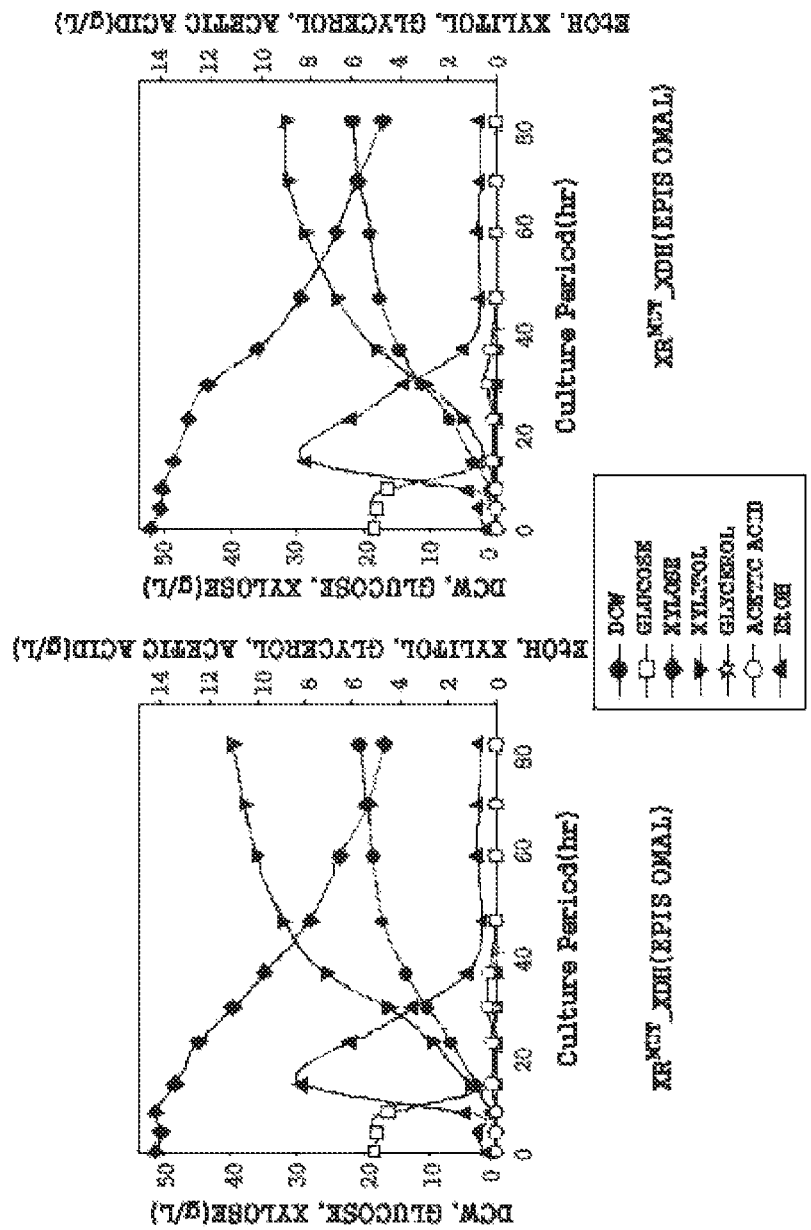
FIG. 3 is a graph comparing the mutated XR with wild-type XR in view of xylose metabolism level (xylitol production efficiency)

The fermentation results are shown in FIG. 3 and the fermentation using XR$^{mut}$ exhibits superior xylitol production efficiency, as compared to the fermentation using XR$^{WT}$. This is the reason that XR$^{mut}$ uses NADH wherein its amount present in the body is greater than NADPH. The ultimate effects of XR$^{MUT}$ on the production of ethanol as well as xylitol cannot be significantly confirmed without additionally over-expressing XK, since XK is present in a low titer in the D452-2/pXR$^{MUT}$/pXDH strain.

Example 3

Fermentation of Ethanol Using SX2, SX3 and SX5 Strains Produced in Example 1

Among the strains produced in Example 1, SX2, SX3 and SX5 are used to ferment ethanol.

SX2 is a strain into which XR$^{mut}$ and XDH are integrated into the genome via homologous recombination, and SX3 is a strain additionally integrated into the delta sequence on the genome to increase ethanol production efficiency for SX2. In addition, SX5 is a strain in which transaldolase 1 (TAL1) is additionally over-expressed to improve the metabolic rate of the pentose phosphate pathway for SX3.

A multi fermentation bath (B.Brown Corp.) with a size of 1 L was used for fermentation and operation volume was 500 mL. The fermentation bath was maintained at a temperature of 30° C. and a fermentation solution was maintained at pH of 5.5. The fermentation was carried out using microaerobic fermentation wherein stirring is performed at a rate of 300 rpm and aeration is performed at a rate of 0.1 vvm.

The microaerobic fermentation results of SX2, SX3 and SX5 strains are shown in Table 2 below (See FIG. 4).

TABLE 2

Microaerobic fermentation results of SX2, SX3 and SX5

Figure 4:
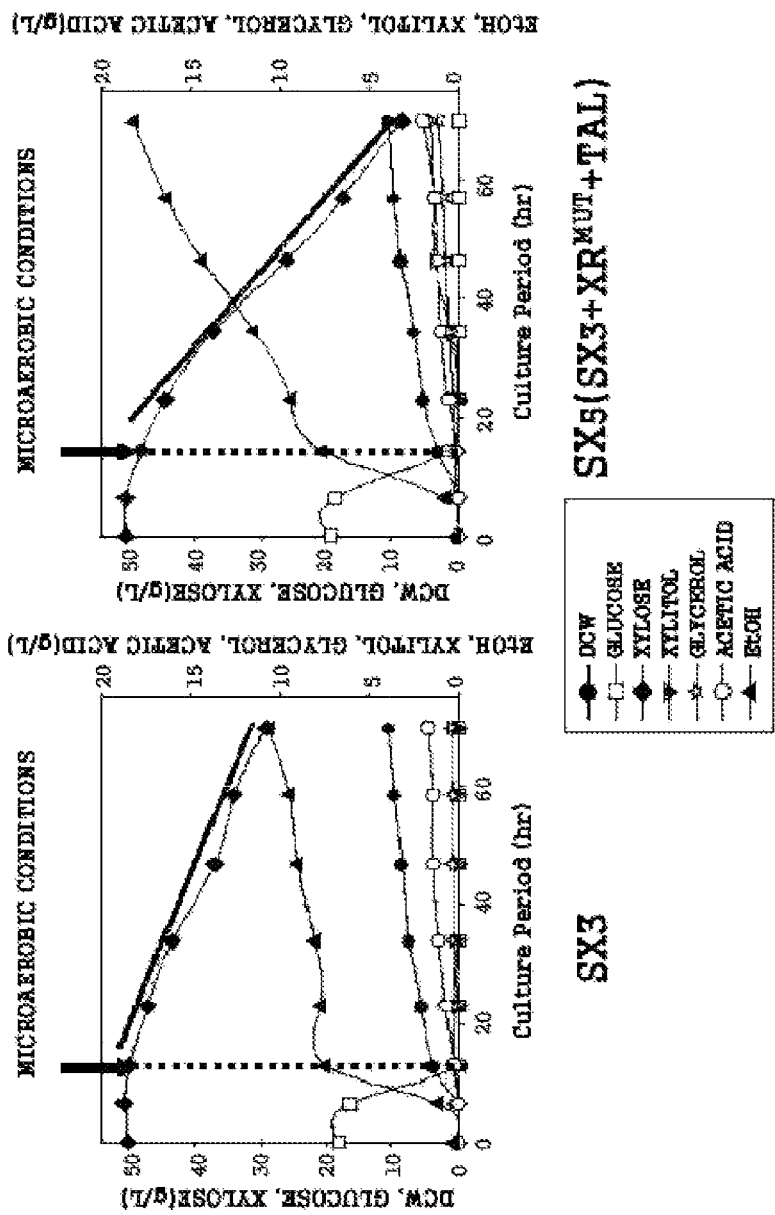
FIG. 4 is a graph comparing the SX3 strain with the SX5 strain in view of ethanol fermentation results.

| Strains | Xylose consumption rate (g/L · hr) | Final ethanol concentration (g/L) | Ethanol production efficiency (g/L · hr) | Yield (g/g (product/xylose)) Ethanol | Xylitol | |
|---|---|---|---|---|---|---|
| SX2 | 0.14 | 7.0 | 0 | 0 | 0.29 | |
| SX3 | 0.38 | 10.7 | 0.06 | 0.17 | 0 | See |
| SX5 | 0.79 | 18.3 | 0.19 | 0.25 | 0.04 | FIG. 4 |

1) SX2: YIpXR$^{MUT}$ – XDH$^{WT}$
2) SX3: SX2 + delta XK
3) SX5: SX3 + YEpXR + pTAL As can be seen from Table 2, the SX3 strain exhibited about 2.7-fold higher xylose consumption rate and about 500-increased final ethanol concentration, as compared to the SX2 strain.

Meanwhile, the SX5 strain wherein XR and XDH enzymes are incorporated and expressed, and XK and TAL1 enzymes are over-expressed, exhibited about a 2-fold increase in xylose consumption rate and an 80%-increased final ethanol concentration, as compared to the SX3 strain. The SX5 strain exhibited a 3-fold increase in ethanol production efficiency and a 47%-increase in yield, as compared to the SX3 strain.

Example 4

Ethanol Fermentation Using Strain SX5 and SX5:ald6Δ Produced in Example 1

Among strains produced in Example 1, SX5 and SX5:ald6Δ, wherein ALD6 genes are removed from the SX5, were used to ferment ethanol.

A multi fermentation bath (B.Brown Corp.) with a size of 1 L was used for fermentation and operation volume was 500 mL. The fermentation bath was maintained at a temperature of 30° C. and a fermentation solution was maintained at pH of 5.5.

The fermentation was carried out using microaerobic fermentation wherein stirring is performed at a rate of 200 rpm and aeration is performed at a rate of 0.06 vvm.

Figure 5:
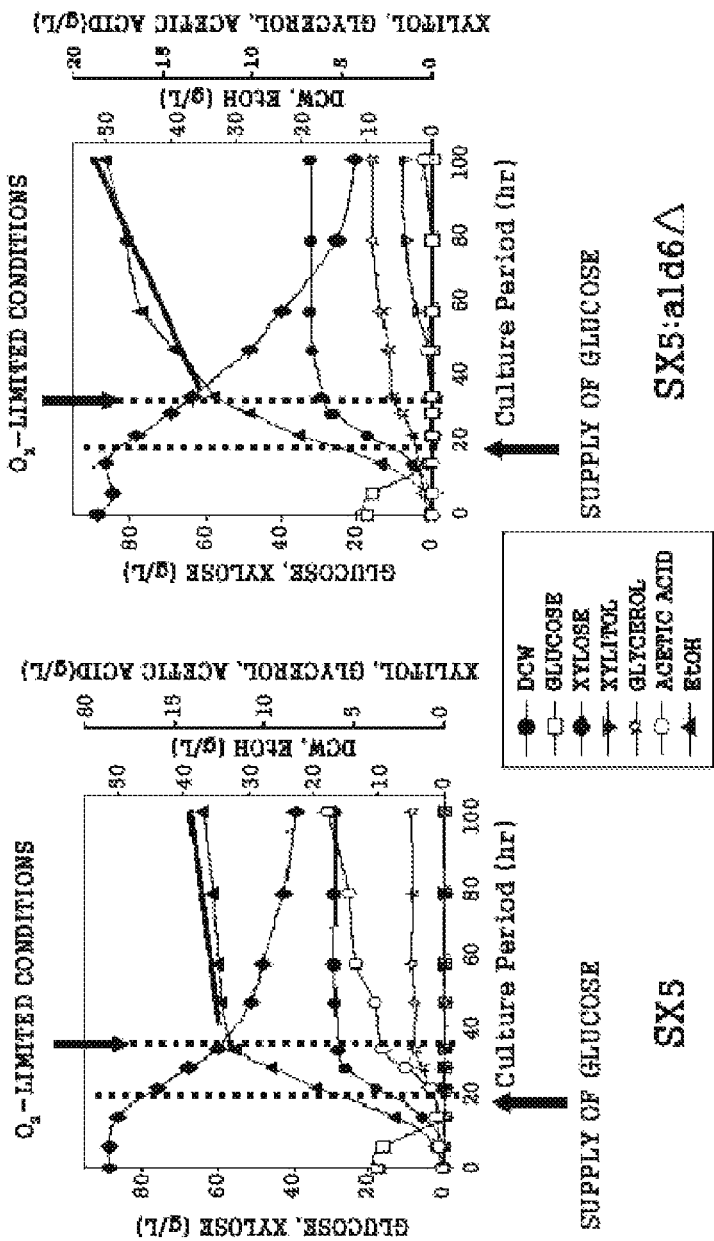
FIG. 5 is a graph comparing SX5:ald6Δstrain, wherein the production of acetic acid is inhibited, with SX5 strain in view of ethanol fermentation results.

$O_2$-limited fermentation results of SX5 and SX5:ald6Δ strains are shown in Table 3 below (See FIG. 5).

TABLE 3

$O_2$-limited fermentation results of SX5 and SX5:ald6Δ strains

| Strains | Xylose consumption rate (g/L · hr) | Final ethanol concentration (g/L) | Ethanol production efficiency (g/L · hr) | Yield (g/g (product/xylose)) Ethanol | Yield (g/g (product/xylose)) Acetic acid | |
|---|---|---|---|---|---|---|
| SX5 | 0.31 | 36.9 | 0.07 | 0.23 | 0.15 | See |
| SX5:ald6Δ | 0.65 | 50.1 | 0.25 | 0.39 | 0.01 | FIG. 4 |

1) SX5: SX3 + YEpXR + pTAL(SX3: SX2 + delta XK, SX2: YIpXR$^{MUT}$ – XDH$^{WT}$)
2) SX5: ald6Δ is obtained by removing ALD6 genes from SX5 strain.

The SX5:ald6Δ strain wherein acetaldehyde dehydrogenase encoding ALD6 genes is fragmented from recombinant yeast in order to minimize acetic acid inhibiting cell growth and ethanol fermentation, exhibited 35% increased final ethanol concentration and 70%-increased ethanol production efficiency, as compared to the SX5 strain, as shown in Table 3 above.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for producing ethanol from xylose using recombinant *Saccharomyces cerevisiae*, the method comprising:
   transforming the recombinant *Saccharomyces cerevisiae* to express NADH-preferring xylose reductase (XR) to convert xylose into xylitol using NADH as a cofactor;
   transforming the recombinant *Saccharomyces cerevisiae* to express xylitol dehydrogenase (XDH) to convert xylitol into xylulose using NAD$^+$ as a cofactor;
   transforming the recombinant *Saccharomyces cerevisiae* to over-express xylulokinase (XK) to convert xylulose into xylulose 5-phosphate; and
   transforming the recombinant *Saccharomyces cerevisiae* to over-express transaldolase 1 (TAL1) to convert sedoheptulose 7-phosphate and glyceraldehyde 3-phosphate into erythrose 4-phosphate and fructose 6-phosphate,
   wherein the recombinant *Saccharomyces cerevisiae* is transformed to entirely or partially fragmentize acetaldehyde dehydrogenase encoding gene ALD6 to disrupt expression on acetaldehyde dehydrogenase that converts acetaldehyde into acetic acid.

2. The method of claim 1, wherein a gene encoding the xylose reductase (XR) or xylitol dehydrogenase (XDH) is integrated into the genome of the *Saccharomyces cerevisiae*.

3. The method of claim 1, wherein a gene encoding the xylitol dehydrogenase (XDH) is integrated into the delta sequence on the genome of the *Saccharomyces cerevisiae*.

4. The method of claim 1, wherein the production of ethanol is carried out by $O_2$-limited fed-batch fermentation.

* * * * *